United States Patent
Chang et al.

(10) Patent No.: US 8,442,628 B2
(45) Date of Patent: May 14, 2013

(54) DIFFERENTIAL VOLTAGE SENSING METHOD

(75) Inventors: Wen Ying Chang, Taoyuan County (TW); Cheng Hung Chang, Taichung (TW); Ying Ju Chen, Tainan County (TW)

(73) Assignee: Industrial Technology Research Institute, Hsinchu (TW)

( * ) Notice: Subject to any disclaimer, the term of this patent is extended or adjusted under 35 U.S.C. 154(b) by 0 days.

(21) Appl. No.: 13/447,573

(22) Filed: Apr. 16, 2012

(65) Prior Publication Data

US 2012/0194268 A1 Aug. 2, 2012

Related U.S. Application Data

(62) Division of application No. 12/784,646, filed on May 21, 2010.

(30) Foreign Application Priority Data

Feb. 25, 2010 (TW) .............................. 99105410 A

(51) Int. Cl.
- A61B 5/04 (2006.01)
- A61B 5/0402 (2006.01)
- A61B 5/0476 (2006.01)
- A61B 5/0488 (2006.01)
- A61B 5/05 (2006.01)
- A61B 5/053 (2006.01)
- H03F 3/45 (2006.01)

(52) U.S. Cl.
USPC ........... 600/547; 600/509; 600/546; 600/544; 330/260

(58) Field of Classification Search .................. 600/509, 600/544, 546, 547; 330/260
See application file for complete search history.

(56) References Cited

U.S. PATENT DOCUMENTS

| | | | | |
|---|---|---|---|---|
| 3,802,419 A * | 4/1974 | Yates | ............................. | 600/536 |
| 4,320,351 A * | 3/1982 | Brown et al. | .................. | 330/260 |
| 4,760,595 A * | 7/1988 | Arai | ............................. | 379/385 |
| 5,873,838 A * | 2/1999 | Mogi | ............................ | 600/509 |
| 6,008,696 A * | 12/1999 | Smith | ........................... | 330/260 |
| 6,016,446 A * | 1/2000 | Belalcazar | ....................... | 607/13 |
| 6,133,787 A * | 10/2000 | Yerkovich et al. | ............... | 330/68 |
| 6,238,338 B1* | 5/2001 | DeLuca et al. | ................. | 600/300 |
| 6,287,328 B1* | 9/2001 | Snyder et al. | .................. | 600/509 |
| 6,292,690 B1* | 9/2001 | Petrucelli et al. | ............. | 600/547 |
| 6,496,721 B1* | 12/2002 | Yonce | ........................... | 600/509 |
| 6,567,698 B2* | 5/2003 | Herleikson | ....................... | 607/5 |
| 6,716,165 B1* | 4/2004 | Flanders et al. | ............... | 600/301 |
| 6,839,587 B2* | 1/2005 | Yonce | ........................... | 600/509 |
| 6,950,694 B2* | 9/2005 | Yonce | ........................... | 600/509 |
| 7,226,418 B2* | 6/2007 | Kim | ............................. | 600/485 |

(Continued)

Primary Examiner — Sean P Dougherty
Assistant Examiner — Michael C Stout
(74) Attorney, Agent, or Firm — WPAT, P.C.; Anthony King

(57) ABSTRACT

A differential voltage sensing method for achieving input impedance matching comprises the steps of: providing a first bio-potential signal to a first variable resistor for generating a first signal; providing a second bio-potential signal to a second variable resistor for generating a second signal; differentially amplifying first and second signals for generating a third signal; selecting an operation band of the third signal for generating first and second logic signals; and dynamically adjusting one of the impedances of the first and second variable resistors according to the first and second logic signals, wherein each of the first and second bio-potential signals has a common signal voltage level and a differential signal voltage level.

7 Claims, 4 Drawing Sheets

U.S. PATENT DOCUMENTS

| | | | |
|---|---|---|---|
| 2001/0025139 A1* | 9/2001 | Pearlman | 600/301 |
| 2003/0018361 A1* | 1/2003 | Herleikson | 607/5 |
| 2004/0077961 A1* | 4/2004 | Yonce | 600/509 |
| 2005/0062530 A1* | 3/2005 | Bardsley et al. | 330/136 |
| 2006/0058694 A1* | 3/2006 | Clark et al. | 600/509 |
| 2007/0129776 A1* | 6/2007 | Robins et al. | 607/88 |
| 2008/0004536 A1* | 1/2008 | Baxi et al. | 600/509 |
| 2009/0067545 A1* | 3/2009 | Chu | 375/316 |
| 2010/0041975 A1* | 2/2010 | Chen et al. | 600/393 |
| 2010/0117736 A1* | 5/2010 | Liao | 330/260 |
| 2011/0025418 A1* | 2/2011 | Aram | 330/253 |
| 2011/0245702 A1* | 10/2011 | Clark et al. | 600/523 |
| 2011/0267144 A1* | 11/2011 | Behera et al. | 330/260 |

* cited by examiner

DIFFERENTIAL VOLTAGE SENSING METHOD

BACKGROUND

1. Technical Field

This disclosure relates to a differential voltage sensing system and a method for achieving input impedance matching, and, in particular, to a differential voltage sensing system and method for sensing bio-potential signals.

2. Description of the Related Art

With the increased focus on personal health among people in recent years, and with the increasing life expectancy of the global population, applications for measuring and monitoring bio-potential signals such as the electrocardiogram (ECG) signal, the electroencephalogram (EEG) signal, the electromyogram (EMG) signal, and the electrooculogram (EOG) signal are frequently required, and the related products are increasingly popular. One widely-used bio-potential measurement apparatus measures signals from the human body via external skin patch electrodes adhesively attached to the subject's skin, and monitors physiological conditions of the heart or the brain via recording and further analysis.

The bio-potential signal acquired from the human body is quite small, and is easily subject to interference from the external environment or from other bio-potential signals from the test subject. Therefore, a differential voltage sensing system with a high common mode rejection ratio (CMRR) is suitable for measuring the small bio-potential signals so as to reduce the influence of noise on the measurement of the bio-potential signals. An input signal of the differential voltage sensing system usually has a common mode signal and differential mode signal. The main component of the common mode signal is noise, and the noise can be canceled by a differential amplifying method because the common mode noise signals are substantially equal in amplitude but invert of phase with one another. Therefore, the differential amplifying method can eliminate the common mode noises and amplify the small bio-potential signals.

However, the common mode noise signals cannot be eliminated when the input impedances of the differential voltage sensing system are not equal, and without elimination of the common mode noise signals the electrical signals are easily subject to distortion because of the interference noise. For example, skin morphology or adhesion of the electrode often results in differences of skin-electrode interface impedance so that the input impedances of the differential voltage sensing system are unequal. In particular, effective electrical signals cannot be captured from multi-pole EEG or multi-lead ECG signals when defective electrodes are present.

U.S. Pat. No. 6,208,888 discloses a voltage sensing system with input impedance balancing. The system comprises a feedback controller that adjusts an effective impedance associated with the second electrode according to a differential mode signal, a common mode signal, and an impedance associated with the first electrode. As a result, signals associated with each electrode undergo a similar degree of gain attenuation. However, since the input impedance balancing is achieved by varying the conversion characteristics of the circuit, an oscillatory noise is generated by such arrangement.

U.S. Pat. No. 5,233,985 discloses a cardiac pacemaker employing an operational amplifier output circuit for producing an electrical stimulating pulse. The circuit employs a variable resistor as a load for capturing signals and finds optimal common mode/differential mode matching points for performing signal measurement. However, such method employs manual operation to vary input impedances for matching, and controls signals by a virtual load.

Accordingly, there is a need to provide a differential voltage sensing system and a method for sensing bio-potential signals so that common mode noise signals can be eliminated using dynamic matching of the input impedances.

SUMMARY

The disclosure relates to a differential voltage sensing system and method for using the same. According to one exemplary embodiment, the differential voltage sensing system comprises a first amplifying circuit, first and second variable resistors, a signal capture unit, and a logic control unit. The first variable resistor has an input terminal connected to a first node, an output terminal connected to a first input terminal of the first amplifying circuit, and a control terminal. The second variable resistor has an input terminal connected to a second node, an output terminal connected to a second input terminal of the first amplifying circuit, and a control terminal. The signal capture unit is connected to an output terminal of the first amplifying circuit, and the logic control unit is connected to the signal capture unit, the control terminal of the first variable resistor, and the control terminal of the second variable resistor. The impedances of the first and second variable resistors can be adjusted dynamically according to output signals of the logic control unit so as to achieve input impedance matching.

According to yet another exemplary embodiment, the differential voltage sensing method for achieving input impedance matching comprises the steps of: providing a first bio-potential signal to a first variable resistor for generating a first signal; providing a second bio-potential signal to a second variable resistor for generating a second signal; differentially amplifying first and second signals for generating a third signal; selecting an operation band of the third signal for generating first and second logic signals; and dynamically adjusting one of the impedances of the first and second variable resistors according to the first and second logic signals, wherein each of the first and second bio-potential signals has a common mode signal voltage level and a differential mode signal voltage level.

BRIEF DESCRIPTION OF THE DRAWINGS

The accompanying drawings, which are incorporated in and constitute a part of this specification, illustrate embodiments of the disclosure and, together with the description, serve to explain the principles of the disclosure.

DETAILED DESCRIPTION

Figure 1:
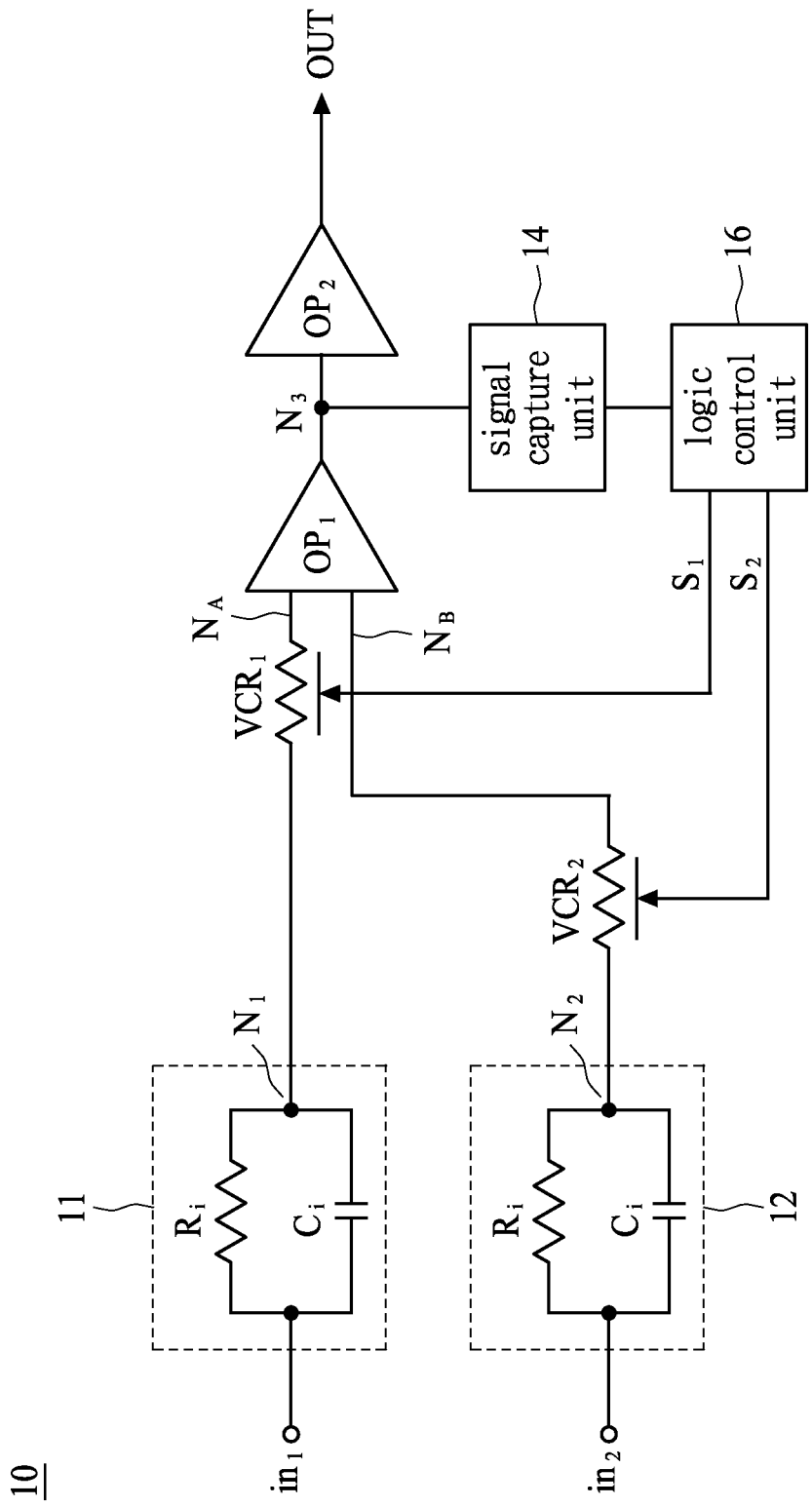
FIG. 1 is a block diagram of a differential voltage sensing system in accordance with an exemplary embodiment.

FIG. 1 is a block diagram of a differential voltage sensing system 10 in accordance with an exemplary embodiment. The differential voltage sensing system 10 comprises first and second electrode interfaces 11 and 12, first and second variable resistors $VCR_1$, $VCR_2$, first and second amplifying circuits $OP_1$ and $OP_2$, a signal capture unit 14, and a logic control unit 16. As shown in FIG. 1, the first electrode interface 11 is connected between an input node $in_1$ and a node $N_1$, while the second electrode interface 12 is connected between an input node $in_2$ and a node $N_2$, wherein the input nodes $in_1$ and $in_2$ are connected to two different positions of a single bio-potential source. The first and second electrode interfaces 11 and 12 are configured to detect bio-potential signals, such as ECG, EOG, EMG, or EOG signals, from a test subject, wherein these bio-potential signals have a common mode signal voltage level and a differential mode signal voltage level. Each of the electrode interfaces 11 and 12 has an effective skin-electrode impedance modeled by an interface resistor R, in parallel with an interface capacitor $C_i$. In addition, the impedances of the electrodes can be varied widely. For example, when the test subject is engaged in physical activity, perspiration may result in reduced resistance due to skin moisture. Alternatively, the resistance may increase due to poor connection or poor adhesion caused by dry electrodes, dry skin, or other skin characteristics common to elderly subjects.

Referring to FIG. 1, the first variable resistor $VCR_1$ has a first input terminal connected to the node $N_1$, a first output terminal connected to a third input terminal $N_A$ of the first amplifying circuit $OP_1$, and a control terminal. The second variable resistor $VCR_2$ has a second input terminal connected to the node $N_2$, a second output terminal connected to a fourth input terminal $N_B$ of the first amplifying circuit $OP_1$, and a control terminal. The variable resistors $VCR_1$ and $VCR_2$ can be voltage controlled resistors whose values are varied according to the voltage level signals of the control terminals. In addition, after receiving input signals through the variable resistors $VCR_1$ and $VCR_2$, the first amplifying circuit $OP_1$ performs a first amplifying processing of the input signals. Subsequently, the second amplifying circuit $OP_2$ connected to the first amplifying circuit $OP_1$ amplifies the signals again to provide to a post stage circuit for signal recording or analysis.

As shown in FIG. 1, the signal capture unit 14 is connected to the first amplifying circuit $OP_1$. In this embodiment, the signal capture unit 14 can be a bandpass filter configured to filter noise out of the band signals from the bio-potential signals, such as 50 Hertz, 60 Hertz, or other environmental noise signals. The logic control unit 16 is connected to the signal capture unit 14 and to the control terminals of the variable resistors $VCR_1$ and $VCR_2$, and is configured to provide control signals $S_1$ and $S_2$ for adjusting the impedances of the variable resistors $VCR_1$ and $VCR_2$. In this embodiment, the logic control unit 16 can be a microcontroller or a single chip processor.

Figure 2:
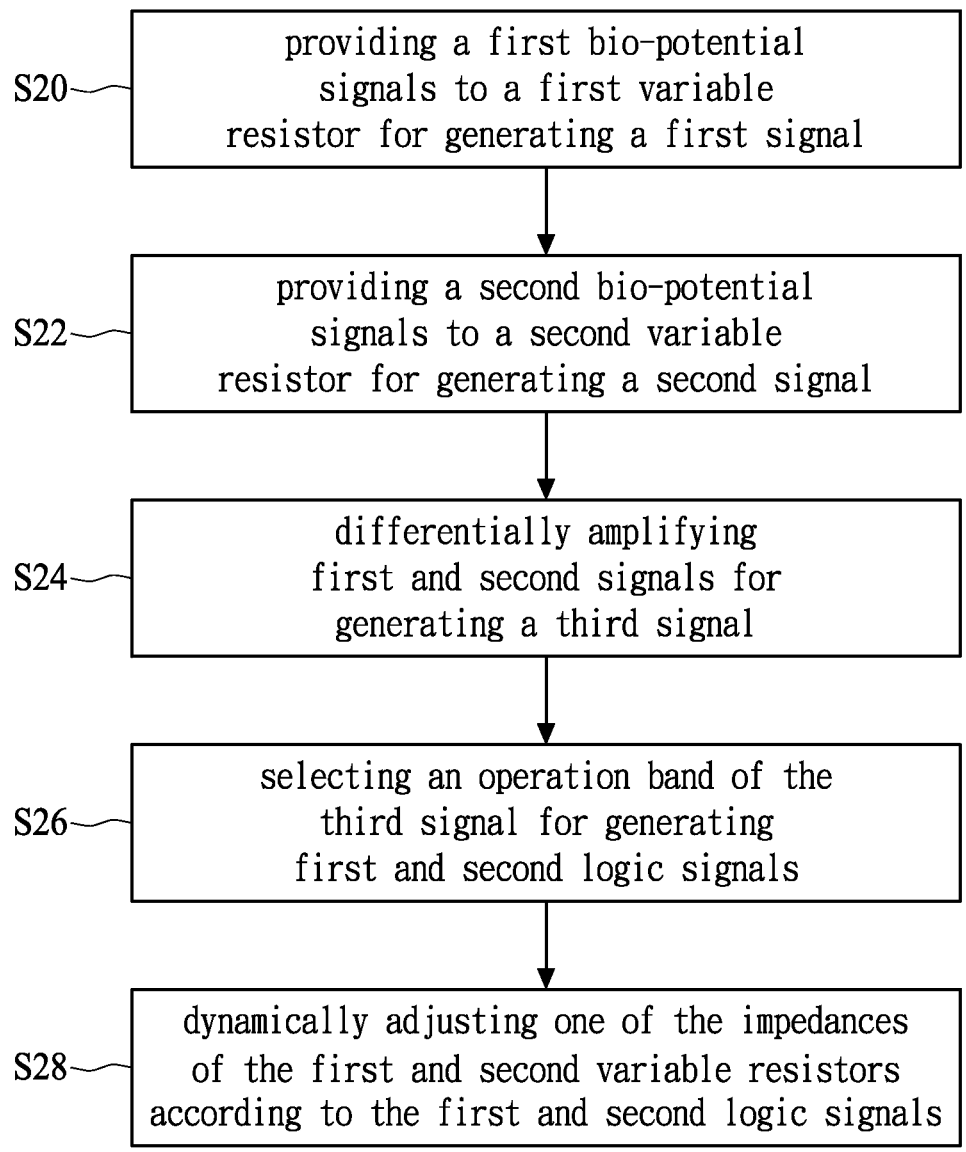
FIG. 2 is a flowchart illustrating an exemplary embodiment of a differential voltage sensing method.

FIG. 2 is a flowchart illustrating an exemplary embodiment of a differential voltage sensing method, wherein the method is employed for achieving input impedance matching. In step S20, a first bio-potential signal is provided to a first variable resistor for generating a first signal. In step S22, a second bio-potential signal is provided to a second variable resistor for generating a second signal. The first and second bio-potential signals have a common mode voltage level and a differential mode voltage level. In step S24, the first and second signals are differentially amplified for generating a third signal. In step S26, the operation band of the third signal is selected for generating first and second logic signals. In step S28, one of the impedances of the first and second variable resistors is dynamically adjusted according to the first and second logic signals. The following describes the details of the differential voltage sensing method of the present disclosure in conjunction with FIG. 1.

First, the first and second bio-potential signals are provided to the first and second variable resistors, respectively, via first and second electrode interfaces 11 and 12. The first and second variable resistors can be resistors $VCR_1$ and $VCR_2$ as shown in FIG. 1. In one embodiment, when the bio-potential signals are ECG signals, the first electrode interface 11 is disposed on or adjacent to the left torso of a test subject, while the second electrode interface 12 is disposed on or adjacent to the right torso of the test subject. As mentioned before, the effective impedances of the electrodes may be different so that the input impedances of the first amplifying circuit $OP_1$ are unequal. In this case, the voltage amplitude of the output terminals $N_3$ will increase and approach saturation. Therefore, one of the impedances of the first and second variable resistors $VCR_1$ and $VCR_2$, e.g., the first variable resistor $VCR_1$, is adjusted. After adjusting the impedance of the first variable resistor $VCR_1$, if the voltage amplitude of the output terminals $N_3$ of the first amplifying circuit $OP_1$ begins to decline, then the impedance of the first variable resistor $VCR_1$ is continuously adjusted until the voltage amplitude of the output terminals $N_3$ reaches a minimum value. The minimum value represents that the differential voltage sensing system 10 has found the optimum input impedance matching point. On the other hand, if adjusting the impedance of the resistor $VCR_1$ does not result in reduction of the voltage amplitude of the output terminals $N_3$ of the first amplifying circuit $OP_1$, then the resistor $VCR_1$ returns to its initial impedance, and the impedance of the resistor $VCR_2$ is adjusted to reduce the voltage amplitude of the output terminals $N_3$. When the voltage amplitude of the output terminals $N_3$ reaches the minimum value, the differential voltage sensing system 10 has found the optimum input impedance matching point.

Referring to FIG. 1, the adjustment of the impedances of the first and second variable resistors $VCR_1$ and $VCR_2$ is implemented via a logic control unit 16. The logic control unit 16 sends signals for controlling the impedances of the variable resistors $VCR_1$ and $VCR_2$ according to an output signal from a signal capture unit 14. In one embodiment, the variable resistors $VCR_1$ and $VCR_2$ can be voltage controlled resistors, and the output signals of the logic control unit 16 can be voltage level signals. Therefore, the impedances of the variable resistors $VCR_1$ and $VCR_2$ can be increased by increasing the voltage levels of the signals $S_1$ and $S_2$, or the impedances of the variable resistors $VCR_1$ and $VCR_2$ can be reduced by decreasing the voltage levels of the signals $S_1$ and $S_2$. In another embodiment, the impedances of the variable resistors $VCR_1$ and $VCR_2$ can be reduced by increasing the voltage levels of the signals $S_1$ and $S_2$, or the impedances of the variable resistors $VCR_1$ and $VCR_2$ can be increased by decreasing the voltage levels of the signals $S_1$ and $S_2$.

Figure 3:
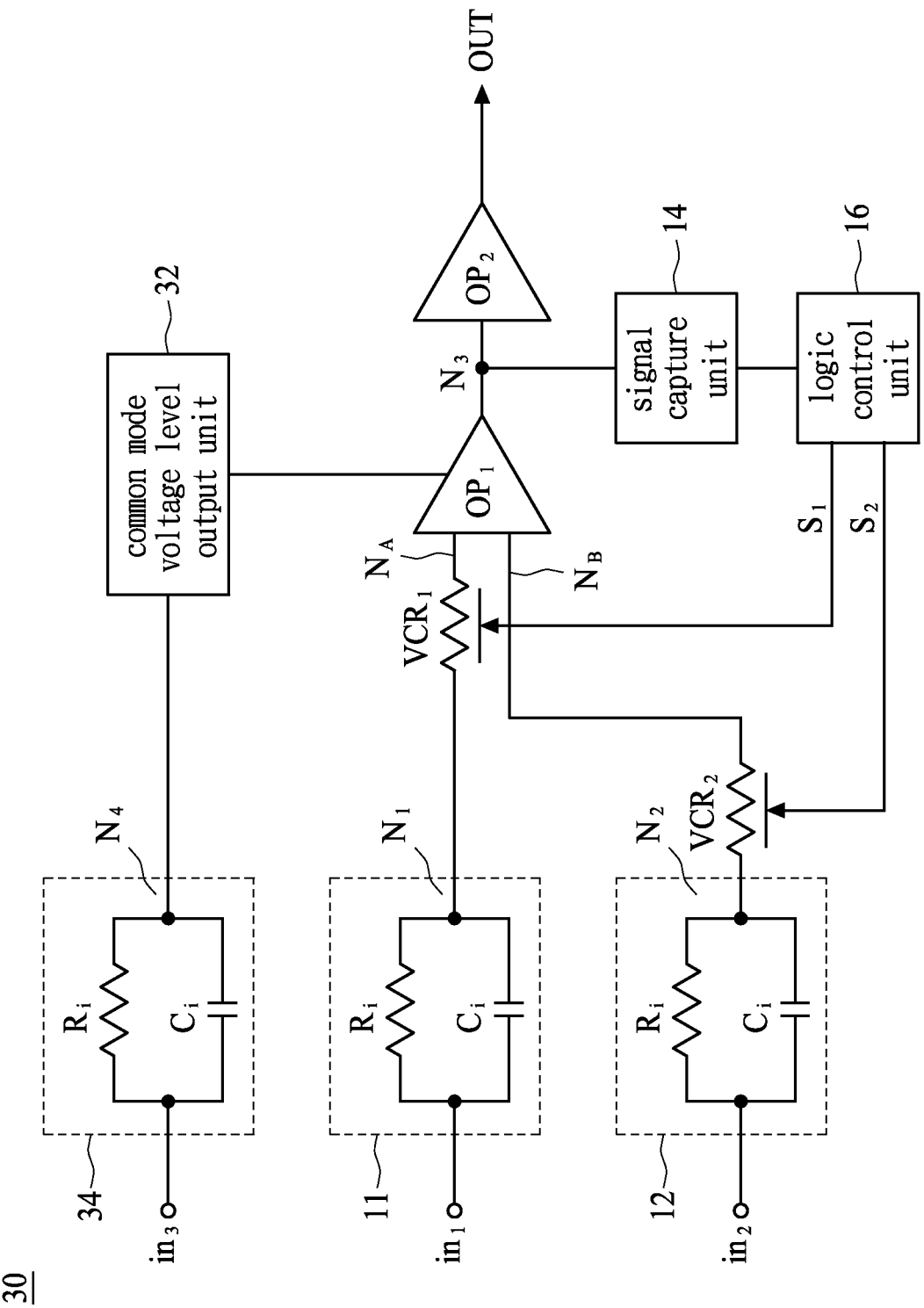
FIG. 3 is a block diagram of a differential voltage sensing system in accordance with another exemplary embodiment.

FIG. 3 is a block diagram of a differential voltage sensing system 30 in accordance with another exemplary embodiment. Referring to FIG. 3, in which like elements of FIG. 1 are shown having like reference designations. Referring to FIG. 3, the differential voltage sensing system 30 comprises a common mode voltage level output unit 32 and a driven right leg (DRL) electrode 34 attached to the test subject's right leg via a node $N_4$. The DRL electrode 34 is configured to reduce the common mode noise signal and improve common mode rejection ratio of the differential voltage sensing system 30.

Figure 4:
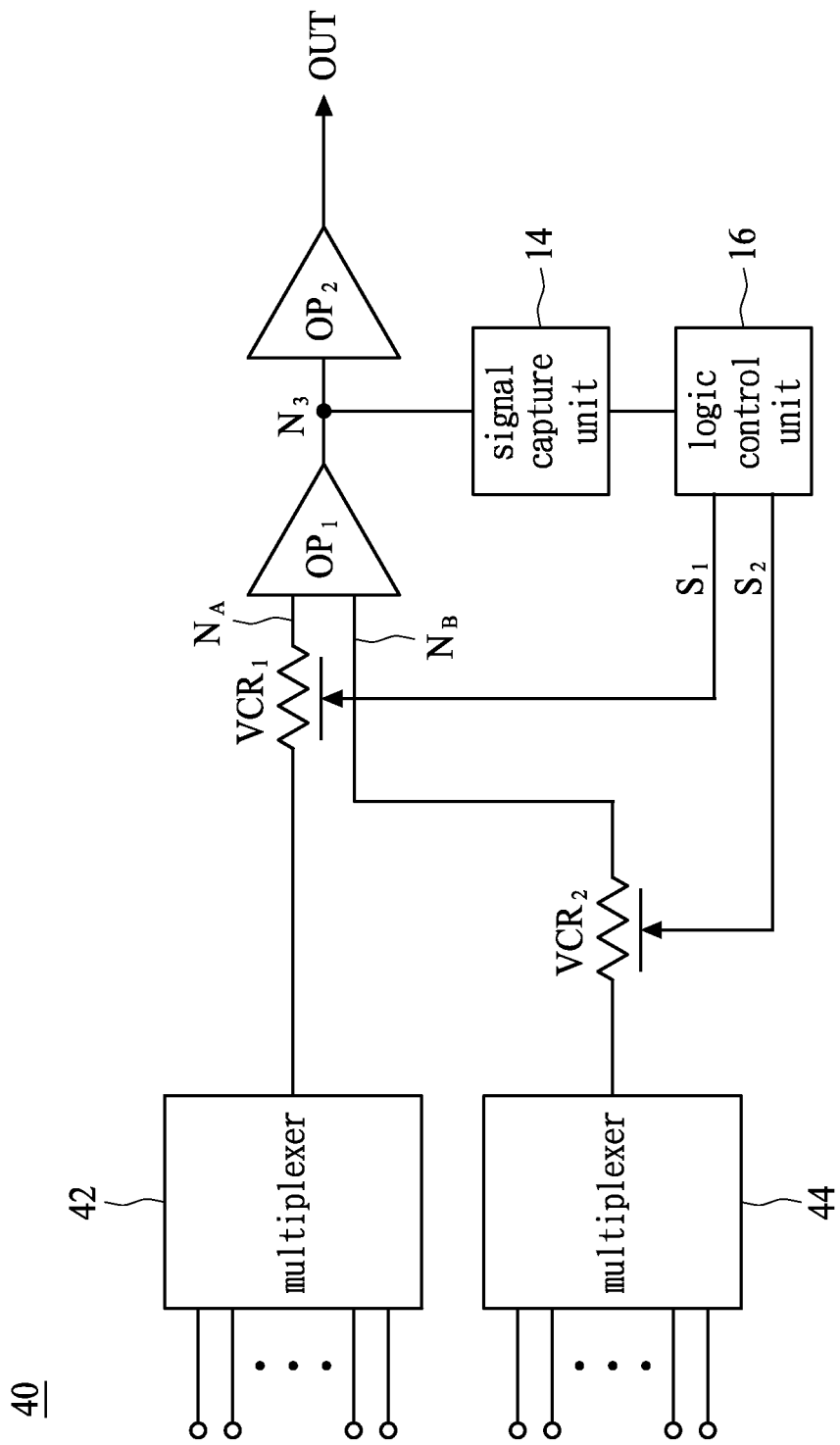
FIG. 4 is a block diagram of a differential voltage sensing system in accordance with another exemplary embodiment.

FIG. 4 is a block diagram of a differential voltage sensing system 40 in accordance with another exemplary embodiment. Like elements of FIG. 1 shown in FIG. 4 having like reference designations. The differential voltage sensing system 40 attaches to the test subject's skin via multi-electrodes or an electrode array. As shown in FIG. 4, multiplexers 42 and 44 are connected to the variable resistors $VCR_1$ and $VCR_2$, respectively, and each multiplexer has a plurality of input terminals connected to a plurality of electrodes. The multiplexers 42 and 44 are configured to selectively connect one of the electrodes to the variable resistors $VCR_1$ and $VCR_2$ according to a scan signal. Subsequently, the logic control unit 16 controls the impedances of the variable resistors $VCR_1$ and $VCR_2$ according to output signals of the signal capture unit 14. The total impedances in the serial path between the input terminal $N_A$ of the first amplifying circuit $OP_1$ and the corresponding electrode, and between the input terminal $N_B$ of the first amplifying circuit $OP_1$ and the corresponding electrode, are subsequently equalized by dynamically adjusting the impedances of the variable resistors $VCR_1$ and $VCR_2$. Accordingly, the common mode noise signals can be significantly reduced, thus protecting output signals from the effects of environmental noise, electrode material, and adhesion state of the electrode.

The above-described exemplary embodiments are intended to be illustrative of the disclosure principle only. Those skilled in the art may devise numerous alternative embodiments without departing from the scope of the following claims.

What is claimed is:

1. A differential voltage sensing method for achieving input impedance matching, comprising the steps of:
    providing a first bio-potential signal to a first variable resistor for generating a first signal;
    providing a second bio-potential signal to a second variable resistor for generating a second signal;
    differentially amplifying first and second signals for generating a third signal;
    selecting an operation band of the third signal for generating first and second logic signals; and
    dynamically adjusting one of the impedances of the first and second variable resistors according to the first and second logic signals;
    wherein each of the first and second bio-potential signals has a common mode signal voltage level and a differential mode signal voltage level.

2. The differential voltage sensing method of claim 1, wherein the first and second bio-potential signals are electrocardiogram signals, electroencephalogram signals, electromyogram signals or electrooculogram signals.

3. The differential voltage sensing method of claim 1, further comprising amplifying the third signal to provide it to a post stage circuit.

4. The differential voltage sensing method of claim 1, further comprising providing the common mode signal voltage level of the third signal to a driven electrode.

5. The differential voltage sensing method of claim 1, further comprising measuring an amplitude of the third signal, wherein if adjusting one of the impedances of the first and second variable resistors cannot reduce the amplitude of the third signal, then the other impedance of the first and second variable resistors is adjusted.

6. The differential voltage sensing method of claim 1, wherein the first and second variable resistors are voltage controlled resistors, and the first and second logic signals are voltage level signals.

7. The differential voltage sensing method of claim 1, further comprising selectively connecting two of a plurality of the electrodes to the first and second variable resistors.

* * * * *